DEFENSIVE PUBLICATION

UNITED STATES PATENT AND TRADEMARK OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent and Trademark Office makes no assertion as to the novelty of the disclosed subject matter.

PUBLISHED NOVEMBER 2, 1976

952 O.G. 6

T952,001

RAPID METHOD FOR DETERMINING DISSOLUTION RATES OF CONTROLLED RELEASE FERTILIZER MATERIALS

Robin M. Scheib and Guerry H. McClellan, Killen, Ala., assignors to Tennessee Valley Authority

Filed Feb. 17, 1976, Ser. No. 658,597
Int. Cl.[2] G01N *21/46, 33/00*
U.S. Cl. 23—230 R
1 Sheet Drawing. 13 Pages Specification

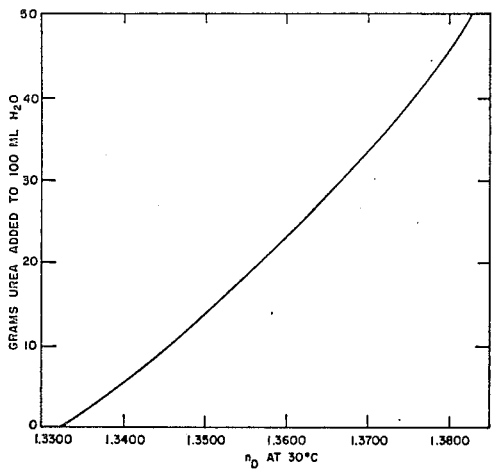

A rapid quality control method for determining the long-term release rate of controlled release fertilizer material. The accepted industry method for testing sulfur-coated urea (SCU) is the seven-day release rate test (SDDR). The instant method was developed to give a release rate which correlated with the SDDR: 50 g. of freshly prepared SCU is put in a cylindrical vessel about 50 mm. in diameter, about 80 mm. high, and having a hemispherical bottom with 100.0 ml. of water. The tip of a probe-type ultrasonic generator is immersed about 2 to 3 cm. into the water and offset from the vertical center line of the vessel about 10 mm. The slurry is subjected to 1.0 minute (.5 to 2 minutes) of ultrasonic vibration at 20,000 Hz. (10,000 Hz. to about 100,000 Hz.) at 200 watts; the slurry is then transferred to a 600-ml. Erlenmeyer flask which is attached to a wrist action shaker such that the bottom half is submerged in a 70° C. (60° C. to 80° C.) water bath and shaken for 10.0 minutes. The refractive index of a filtered portion of the slurry is determined; the urea released can be determined from an appropriately constructed graph or from the formula:

$$\frac{10649.863-16630.54622n_D+6482.844917n_D^2}{50-\%\text{ coating weight}/2}\times 100=\%\text{ urea released}$$

where $n_D$=refractive index of urea solution.

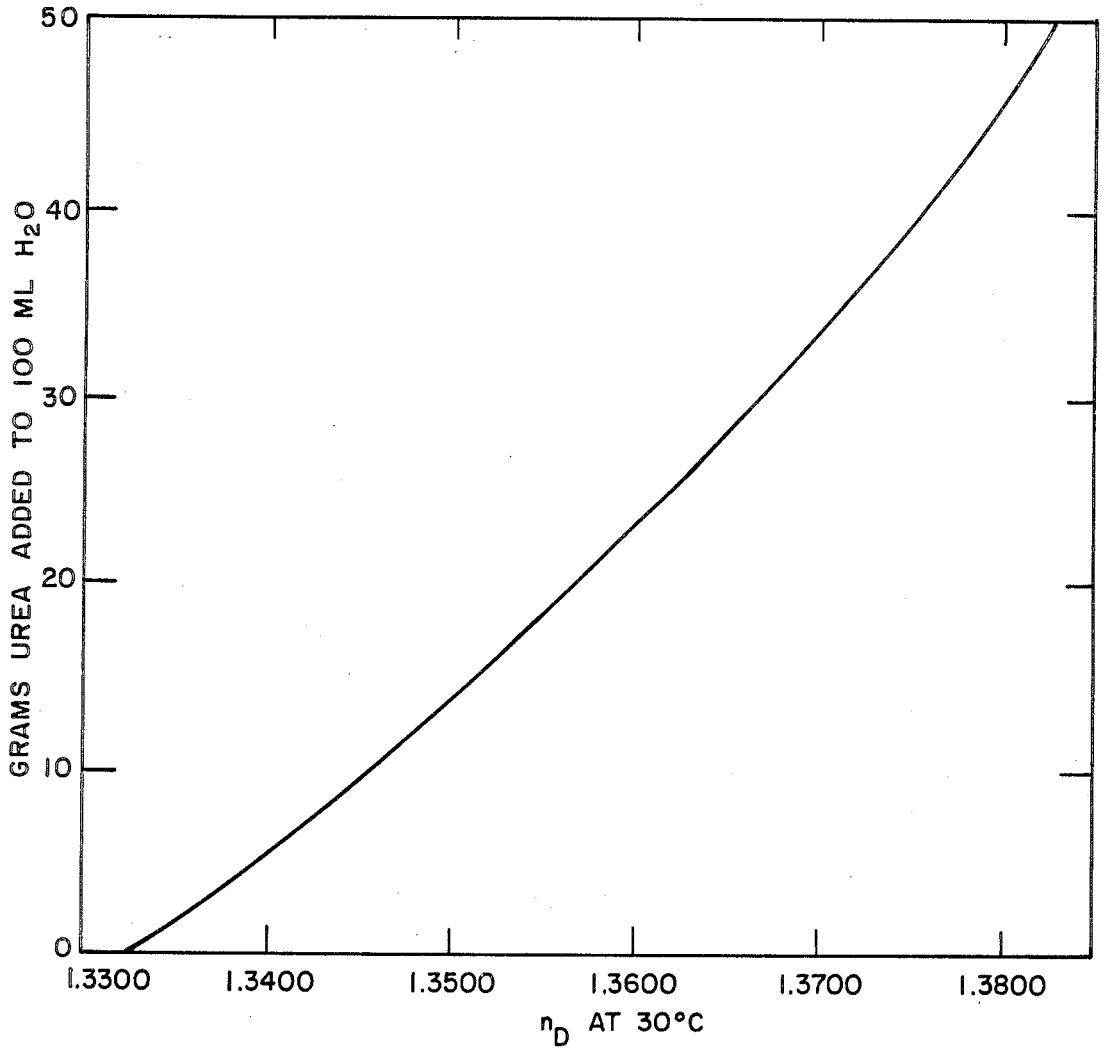

RAPID METHOD FOR DETERMINING DISSOLUTION RATES OF CONTROLLED RELEASE FERTILIZER MATERIALS
Original Filed Feb. 17, 1976